United States Patent [19]

Sprenger, deceased

[11] 4,163,859
[45] Aug. 7, 1979

[54] PHENOXYLDIALKYL ACETIC ACIDS AND ESTERS

[75] Inventor: William K. Sprenger, deceased, late of Arlington Heights, Ill., by Barbara A. Sprenger, personal representative

[73] Assignee: G. D. Searle & Co., Skokie, Ill.

[21] Appl. No.: 816,237

[22] Filed: Jul. 18, 1977

[51] Int. Cl.$^2$ .................... C07C 65/20; C07C 69/95; A61K 31/19; A61K 31/235
[52] U.S. Cl. .................................. 560/53; 562/464; 424/308; 424/317
[58] Field of Search ....................... 560/53; 260/520 C; 562/464

[56] References Cited

U.S. PATENT DOCUMENTS

| | | | |
|---|---|---|---|
| 3,558,612 | 1/1971 | Kuhn et al. | 260/520 C |
| 3,598,860 | 8/1971 | Griot | 260/520 C |
| 3,948,973 | 4/1976 | Phillips | 560/53 |
| 3,968,143 | 7/1976 | Schacht et al. | 260/520 C |

FOREIGN PATENT DOCUMENTS 43-9539  4/1968  Japan ........................................ 560/53

*Primary Examiner*—Joseph E. Evans
*Attorney, Agent, or Firm*—Dragan J. Karadzic; J. J. McDonnell

[57] ABSTRACT

The present invention encompasses compounds of the formula

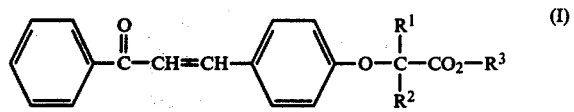

wherein $R^1$ and $R^2$ are independently an alkyl radical containing from 1 to 2 carbon atoms and $R^3$ is hydrogen or an alkyl radical containing from 1 to 7 carbon atoms, sodium, potassium, or ammonium cation. The compounds of the present invention are prepared by the condensation of alkyl(4-formylphenoxy)-2,2-dialkylacetate with acetophenone in basic medium. These compounds are potent hypolipemic agents as well as antifungal and antibacterial agents.

3 Claims, No Drawings

PHENOXYLDIALKYL ACETIC ACIDS AND ESTERS

The present invention encompasses compounds of the formula

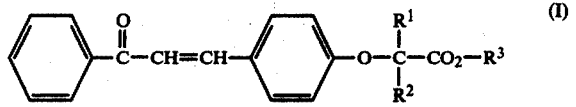

wherein $R^1$ and $R^2$ are independently an alkyl radical containing from 1 to 2 carbon atoms, and $R^3$ is hydrogen or an alkyl radical containing from 1 to 7 carbon atoms, sodium, potassium, or ammonium cation.

The alkyl radicals containing from 1 to 2 carbon atoms denoted in the above formula are methyl or ethyl.

The alkyl radicals containing from 1 to 7 carbon atoms denoted in the above formula are exemplified by methyl, ethyl, propyl, butyl, pentyl, hexyl, heptyl, and the branch chain isomers thereof.

A preferred embodiment of the present invention is represented by the formula

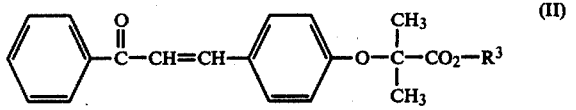

wherein $R^3$ is defined as hereinbefore.

The compounds of the present invention are structurally distinct from compounds of the most closely related art. For example, U.S. Pat. No. 3,558,612 describes 4-(arylcarbonylalkanyl)phenoxyacetic acid derivatives. The compounds of the present invention are particularly distinct from the compounds in U.S. Pat. No. 3,558,612 in that the compounds in the present invention are derivatives of dialkylacetic acid instead of acetic acid.

Compounds of the present invention are conveniently prepared as set out in Scheme I wherein $R^1$, $R^2$ and $R^3$ are as previously defined.

Scheme I

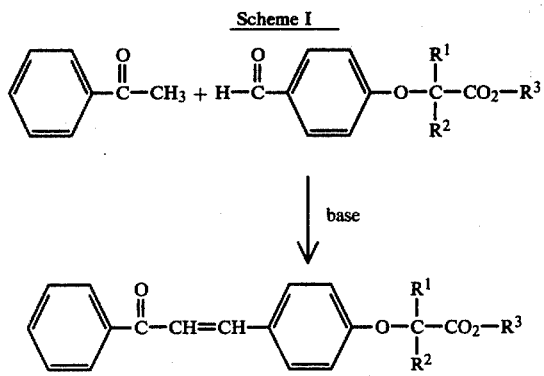

Thus, the condensation of alkyl(4-formylphenoxy)-2,2-dialkylacetate described in U.S. Pat. No. 3,842,120 with acetophenone in basic medium provides compounds of the present invention.

In this manner 7.1 parts of ethyl(4-formylphenoxy)-2,2-dimethylacetate and 4.7 parts of acetophenone in 10 parts by volume of ethanol containing 0.01 part of sodium ethyl are reacted for 2 hours. This reaction mixture is quenched with 100 parts of cold water and extracted with ether. The ether extracts are dried over magnesium sulfate. Filtration of the magnesium sulfate, removal of ether by evaporation at reduced pressure and column chromatography on silica gel provides ethyl 2-[4-(2-benzoylethenyl)phenoxy]-2,2-dimethylacetate melting at 68° to 70° C. Treatment of this ester with alcoholic potassium hydroxide for 2 hours, followed by extraction with ether, and acidification with dilute hydrochloric acid provides a precipitate which is 2-[4-(2-benzoylethenyl)phenoxy]-2,2-dimethylacetic acid.

Hypolipemic activity of compounds of the present invention are illustrated by the following test:

The oral hypolipemic activity of ethyl 2-[4-(2-benzoylethenyl)phenoxy]-2,2-dimethylacetate was evaluated in the male rat using clofibrate salt under the trademark of Atromid-S ® as a reference compound.

Male rats of the COBS-CD strain from Charles River Breeding Laboratories were used in this test. Rats weighed between 300 and 360 grams initially and were fed Purina Rat Chow ®. Rats were housed in pairs and allowed free access to food and water.

Male rats were divided into groups of eight rats. Ethyl 2-[4-(2-benzoylethenyl)-2,2-dimethylacetate in propylene glycol, was administered intragastrically at the dose of 150 mg/kg/day once daily for 6 days to a group of rats. A control group of rats received only propylene glycol. On the last day of treatment, all rats were fasted overnight prior to collection of blood from the abdominal aorta. Blood serum was analyzed for serum total cholesterol (1) and triglyceride (2). Test results were evaluated in the two-tailed Student's t-test to determine whether differences for cholesterol and triglyceride from treated and control groups of rats were statistically significant at the $p \leq 0.05$ level. Data are represented in Table I for serum total cholesterol and triglyceride for ethyl 2-[4-(2-benzoylethenyl)-phenoxy]-2,2-dimethylacetate and the sodium salt of Atromid-S ®. Results are presented as percent of control which has been set at 100%. The results indicate that ether 2-[4-(2-benzoylethyl)phenoxy]-2,2-dimethylacetate exhibits oral lipid lowering activity in the male rat at a dose of 150 mg/kg/day.

Table 1

Effect of Ethyl 2-[4-(2-benzoylethenyl)phenoxy]-2,2-dimethylacetate and Atromid-S Na Salt, on Blood Serum Total Cholesterol and Triglyceride on Rats

| Treatment | Dose mg/kg/day | Blood Serum Lipids Cholesterol %[a] | Triglyceride % |
|---|---|---|---|
| Control | — | 100 | 100 |
| Ethyl 2-[4-(2-benzoylethenyl)-phenoxy]-2,2-dimethylacetate | 150 | 75[b] | 59[b] |
| Control | — | 100 | 100 |
| Atromid-S Salt | 100 | 74[b] | 97 |

[a]Results are expressed as percent of control with the control values designated as 100%
[b]Statistically significant difference from control at $p \leq 0.05$ Further indication of hypolipemic utility of the compounds of the present invention is their ability to inhibit in vitro the conversion of $^{14}C$-hydroxymethylglutaryl-CoA to $^{14}C$-mevanolactone. For example, ethyl 2-[4-(2-benzoylethenyl)phenoxy]-2,2-dimethylacetate inhibits this conversion by 61% as compared to controls at $10^{-3}$ molar.

In addition, compounds of the present invention inhibit in vitro the incorporation of $^{14}$C-acetate into lipids, non-suponifiable steriles, and fatty acids. For example, the above compound inhibits 70% as compared to controls at $10^{-3}$ molar.

In addition, compounds of the present invention are antibacterial and antifungal as evidenced by their activity against Erwinia and *Trichophyton mentagrophytes*, respectively. Thus, ethyl 2-[4-(2-benzoylethenyl)-phenoxy]-2,2-dimethylacetate prevents growth of Erwinia during an incubation period of 24 hours at 37° C. at 1000 mcg/ml and prevents growth of *Trichophyton mentagrophytes* during an incubation period of between 5 and 7 at 1000 mcg/ml.

Undecylenic acid, a clinically useful antifungal, is active against *Trichophyton mentagrophytes* under similar conditions.

The following examples are presented to further illustrate the present invention. They should not be construed as limiting it either in spirit or in scope. In these examples quantities are indicated in parts by weight unless parts by volume is specified, and temperatures are indicated in degrees Centigrade (°C.). The relationship between parts by weight and parts by volume is the same as that existing between grams and milliliters.

EXAMPLE 1

7.1 Parts of ethyl (4-formylphenoxy)-2,2-dimethylacetate described in U.S. Pat. No. 3,842,120 and 4.7 parts of acetophenone in 10 parts by volume of ethanol containing 0.01 part of sodium ethyl are reacted for 2 hours. This reaction mixture is quenched with 100 parts of cold water and extracted with ether. The ether extracts are dried over magnesium sulfate. Filtration of the magnesium sulfate, removal of the ether by evaporation at reduced pressure, and column chromatography on silica gel provides ethyl 2-[4-(2-benzoylethenyl)-phenoxy]-2,2-dimethylacetate, melting at 68° to 70° C. This compound has the following structural formula

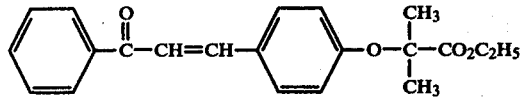

Treatment of the above ester with alcoholic potassium hydroxide for 2 hours, following by extraction with ether, and acidification with dilute hydrochloric acid provides a precipitate which is 2-[4-(2-benzoylethenyl)phenoxyl]-2,2-dimethylacetic acid. This compound has the following structural formula

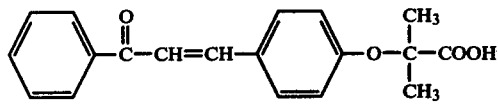

Titration of the above acid with sodium, potassium, or ammonium hydroxide provides the corresponding acid salt.

Reaction of the above acid with diazomethane provides methyl 2-[4-(2-benzoylethenyl)phenoxy]-2,2-dimethylacetate.

EXAMPLE 2

Substitution of an equivalent quantity of ethyl (4-formylphenoxy)-2-ethyl-2-methylacetate for ethyl (4-formylphenoxy)-2,2-dimethylacetate called for in Example 1 and substantial repetition of the procedures detailed therein provides ethyl 2-[4-(2-benzoylethenyl)phenoxy]-2-ethyl-2-methylacetate. This compound has the following structural formula

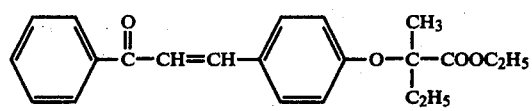

EXAMPLE 3

Substitution of an equivalent quantity of ethyl (4-formylphenoxy)-2,2-diethylacetate for ethyl (4-formylphenoxy)-2,2-dimethylacetate called for in Example 1 and substantial repetition of the procedure detailed therein provides ethyl 2-[4-(2-benzoylethenyl)phenoxy]-2,2-diethylacetate. This compound has the following structural formula

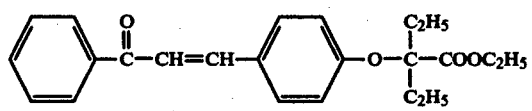

What is claimed is:
1. A compound of the formula

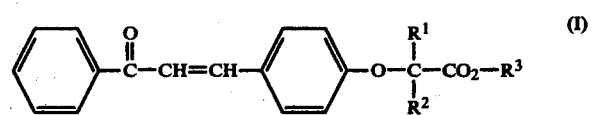

wherein $R^1$ and $R^2$ are independently an alkyl radical containing from 1 to 2 carbon atoms, and $R^3$ is hydrogen or an alkyl radical containing from 1 to 7 carbon atoms, sodium, potassium, or ammonium cation.

2. A compound of the formula

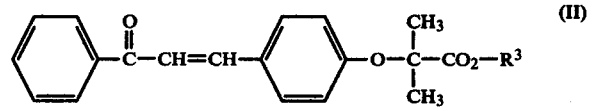

wherein $R^3$ is hydrogen or an alkyl radical containing from 1 to 7 carbon atoms, sodium, potassium, or ammonium cation.

3. A compound which is ethyl 2-[4-(2-benzoylethenyl)phenoxy]-2,2-dimethylacetate.